(12) United States Patent
Karpowicz et al.

(10) Patent No.: US 7,887,510 B2
(45) Date of Patent: Feb. 15, 2011

(54) SUCTION CONTROL APPARATUS AND METHODS FOR MAINTAINING FLUID FLOW WITHOUT COMPROMISING STERILE LINES

(75) Inventors: John Karpowicz, Chester Springs, PA (US); Kevin P. Klocek, Ardmore, PA (US)

(73) Assignee: Boehringer Laboratories, Inc., Phoenixville, PA (US)

( * ) Notice: Subject to any disclaimer, the term of this patent is extended or adjusted under 35 U.S.C. 154(b) by 1441 days.

(21) Appl. No.: 11/007,512

(22) Filed: Dec. 8, 2004

(65) Prior Publication Data
US 2005/0124966 A1 Jun. 9, 2005

Related U.S. Application Data

(60) Provisional application No. 60/527,695, filed on Dec. 8, 2003.

(51) Int. Cl.
*A61M 1/00* (2006.01)
(52) U.S. Cl. ...................... 604/119; 604/118
(58) Field of Classification Search .............. 604/118, 604/119, 323, 324; 433/95, 185; 137/599.16, 137/599.17
See application file for complete search history.

(56) References Cited

U.S. PATENT DOCUMENTS

| | | | | |
|---|---|---|---|---|
| 4,369,785 A | * | 1/1983 | Rehkopf et al. | 604/119 |
| 4,702,733 A | * | 10/1987 | Wright et al. | 604/34 |
| 5,337,780 A | * | 8/1994 | Kee | 137/381 |
| 6,070,582 A | * | 6/2000 | Kee | 128/207.16 |
| 6,142,980 A | * | 11/2000 | Schalk | 604/247 |
| 7,175,612 B2 | * | 2/2007 | Felix et al. | 604/323 |

* cited by examiner

*Primary Examiner*—Nicholas D Lucchesi
*Assistant Examiner*—Laura A Bouchelle
(74) *Attorney, Agent, or Firm*—RatnerPrestia

(57) ABSTRACT

The present invention relates to a device and method to control suction in a patient environment. The device comprises a body portion having an interior chamber adapted for coupling to a source of the vacuum; a valve comprising a shaft rotatably coupled to the body portion; and an actuator coupled to the shaft of the valve. In operation the valve is rotatable between i) a first position in which the vacuum is provided to the interior chamber via the valve at a first predetermined level and ii) a second position in which the vacuum is interrupted to the interior chamber. The actuator is adapted to move between a first position and a second position which increases the vacuum in the interior chamber to a second predetermined level for clearing occluded suction lines in the patient circuit.

20 Claims, 7 Drawing Sheets

SUCTION CONTROL APPARATUS AND METHODS FOR MAINTAINING FLUID FLOW WITHOUT COMPROMISING STERILE LINES

CROSS REFERENCE TO RELATED APPLICATIONS

This application claims priority to provisional application Ser. No. 60/527,695 filed on Dec. 8, 2003.

FIELD OF THE INVENTION

This invention relates generally to medical vacuum devices. More specifically, the present invention relates to devices and methods for monitoring and maintaining constant flow in a patient vacuum circuit without the need to break any patient connections for evaluation or intervention.

BACKGROUND OF THE INVENTION

Suction is widely employed in a Hospital environment to assist health care providers in the care of patients. On its most basic level, suction is used to remove fluids and debris from body cavities and is employed in virtually any location where patient care is needed.

Bodily fluids drawn through these suction lines are not typically of homogenous viscosity and may even be a suspension of both solid and liquid components. Certain applications dictate that very low levels of vacuum (<120 mm Hg) be used to remove these accumulated fluids. Such instances may be found when suctioning the airway and surrounds.

Low levels of vacuum are appropriate from a patient safety standpoint, but these low levels may not create adequate force to pull viscous fluids through the lines. Further, the suction lines are prone to blockage when very viscous fluids, congealed blood, or solid particles enter the vacuum circuit. Certain biological fluids may also congeal inside of the suction lines if the fluid is not constantly moving in the circuit.

The present standard of care for occluded suction lines begins with uncoupling the line downstream of the blockage. A conventional syringe is then used to draw any accumulated debris through the line. This syringe acts as a flow limited vacuum generating device.

Disadvantageously, uncoupling this line creates a vector for micro-organisms to enter the patient circuit. Uncoupling this line also exposes the health care provider and patient to cross contamination from each other or the environment. Each time a blockage occurs valuable time is dedicated to maintaining sterile technique. Further, additional disposable medical waste is also generated by these interventions.

SUMMARY OF THE INVENTION

In view of the shortcomings of conventional systems and methods, the present invention is an apparatus and method which allows health care providers to quickly evaluate if a suction line is occluded.

According to one aspect of the invention the device comprises a body portion having an interior chamber and adapted for coupling to a vacuum source; a valve comprising a shaft rotatably coupled to the body portion; and an actuator coupled to the shaft of the valve, wherein the valve is rotatable between i) a first position in which the vacuum is provided to the interior chamber via the valve at a first predetermined level and ii) a second position in which the vacuum is interrupted to the interior chamber, and the actuator is adapted to move between a first position and a second position which increases the vacuum in the interior chamber to a second predetermined level.

According to another aspect of the invention, the device further comprises a further valve rotatably coupled to the body portion, and an output port coupled to the interior chamber for receiving the first and second predetermined levels of vacuum.

According to a further aspect of the invention, an indicator is coupled to the body portion to display a level of vacuum provided to the output port to indicate a condition of the patient circuit.

According to still another aspect of the invention, the valve comprises a first vacuum circuit including a groove disposed partially around an outside portion of the shaft, such that the groove provides fluid communication between the interior chamber and the source of vacuum when the valve is in the first position; and a second vacuum circuit including a first orifice disposed along at least a portion of the shaft along the longitudinal axis, a second orifice disposed in the shaft oriented transverse to the longitudinal axis and in fluid communication with the first orifice, and a third orifice disposed in the shaft oriented transverse to the longitudinal axis and in fluid communication with the first orifice, such that the second vacuum circuit provides fluid communication between the interior chamber and the source of vacuum when the actuator is in the second.

According to yet another aspect of the invention, the actuator further comprises a shaft coaxially coupled to the shaft of the valve, a first orifice extending from an end of the shaft and at least partially along an interior of the shaft, a circumferential groove disposed along an outside potion of the shaft, a second orifice formed in the circumferential groove, transverse to the first orifice and in fluid communication with the first orifice, such that the actuator provides fluid communication between the interior chamber and the source of vacuum via i) the first orifice, ii) the circumferential groove and iii) the second orifice when the actuator is in the second position.

These and other aspects of the invention are set forth below with reference to the drawings and the description of exemplary embodiments of the invention.

BRIEF DESCRIPTION OF THE DRAWINGS

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawing are the following Figures.

DETAILED DESCRIPTION OF THE INVENTION

The present invention relates to improvements in a mechanical or electromechanical control device and methods used to control suction in a patient environment. The invention provides improvements to the functional regulation characteristics allowing the use of a temporary increase in the level of suction to facilitate the removal of blockages from a suction line. Desirably, this increase in vacuum is both regulated and flow controlled to mitigate any potential harm to the patient. If the suction line is not occluded, operating the present invention will not effect level of vacuum in the patient circuit.

A trained health care provider can easily operate the exemplary device and visually evaluate if fluid flow in the suction line is occluded. If fluid flow is occluded, the health care provider can then operate the exemplary device to remove the blockage from the line. Because any potential blockage isolates the regulated vacuum source from the patient, the increased vacuum generated in the line is not experienced by the patient. Once the blockage is cleared, the flow and/or pressure restricted nature of the present invention will be overridden by the main regulating mechanism and an excessively high vacuum will not be applied to the patient.

Certain design characteristics have been identified as having unique qualities for a suction control used to maintain patient and flowing suction lines in a clinical environment. Among these characteristics are:

1. The exemplary regulator comprises a simple momentary actuator, which will temporarily increase the applied vacuum when depressed. Once the actuator is released, there is no impact on the regulated vacuum setting.
2. The exemplary actuator allows a simple determination of whether or not a suction line is occluded, without breaking sterile technique.
3. The exemplary actuator allows the use of an existing vacuum gauge to determine if a suction line is flowing, without the need for an additional flow gauge.
4. The exemplary actuator allows the temporary application of increased vacuum that is regulated via the relative ratio of two orifices.
5. The exemplary actuator allows the temporary application of increased vacuum that is regulated via a second independent regulator internal to the device.

Figure 1:
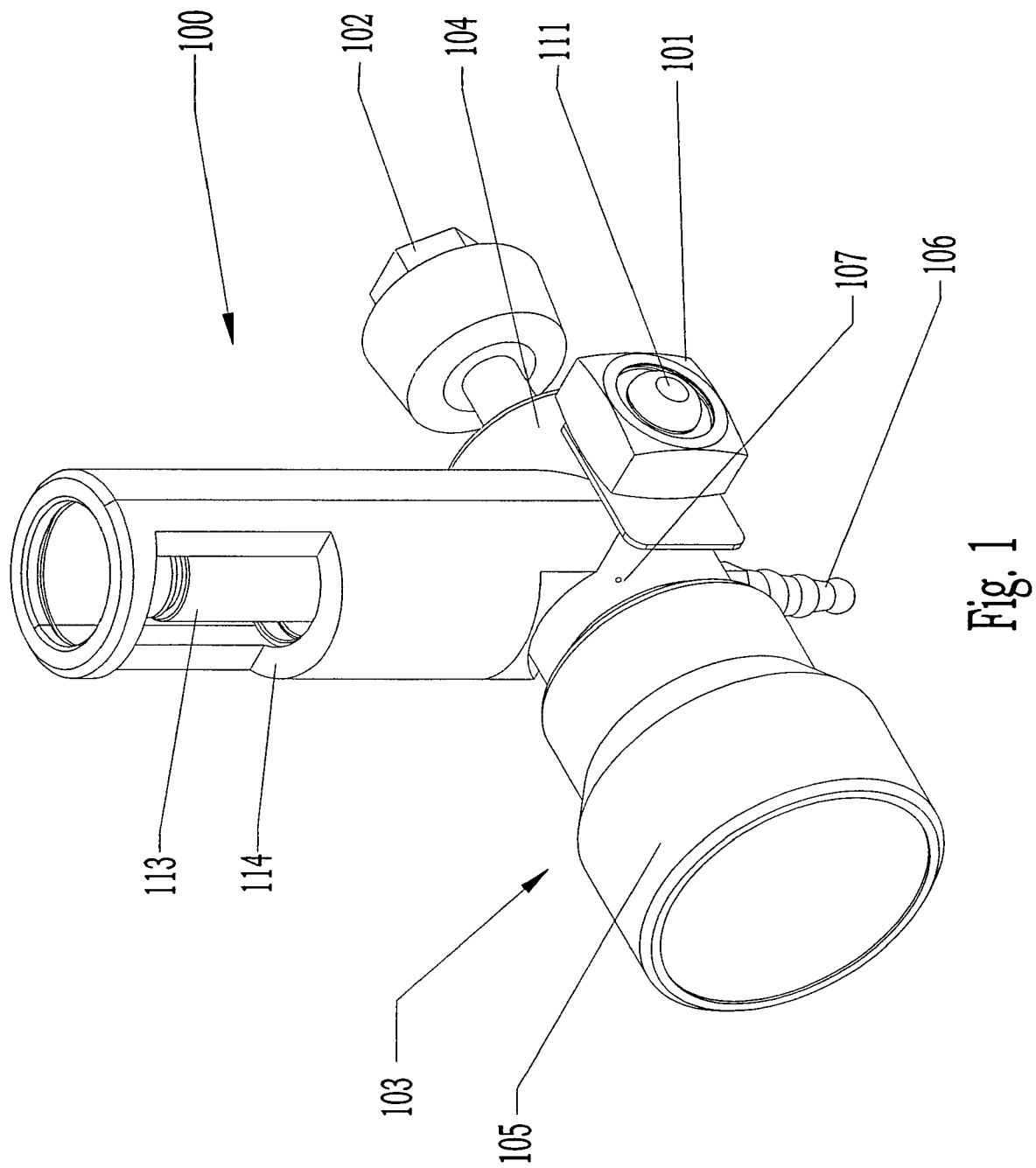
FIG. 1 is perspective view of an exemplary embodiment of the present invention.
Figure 2:
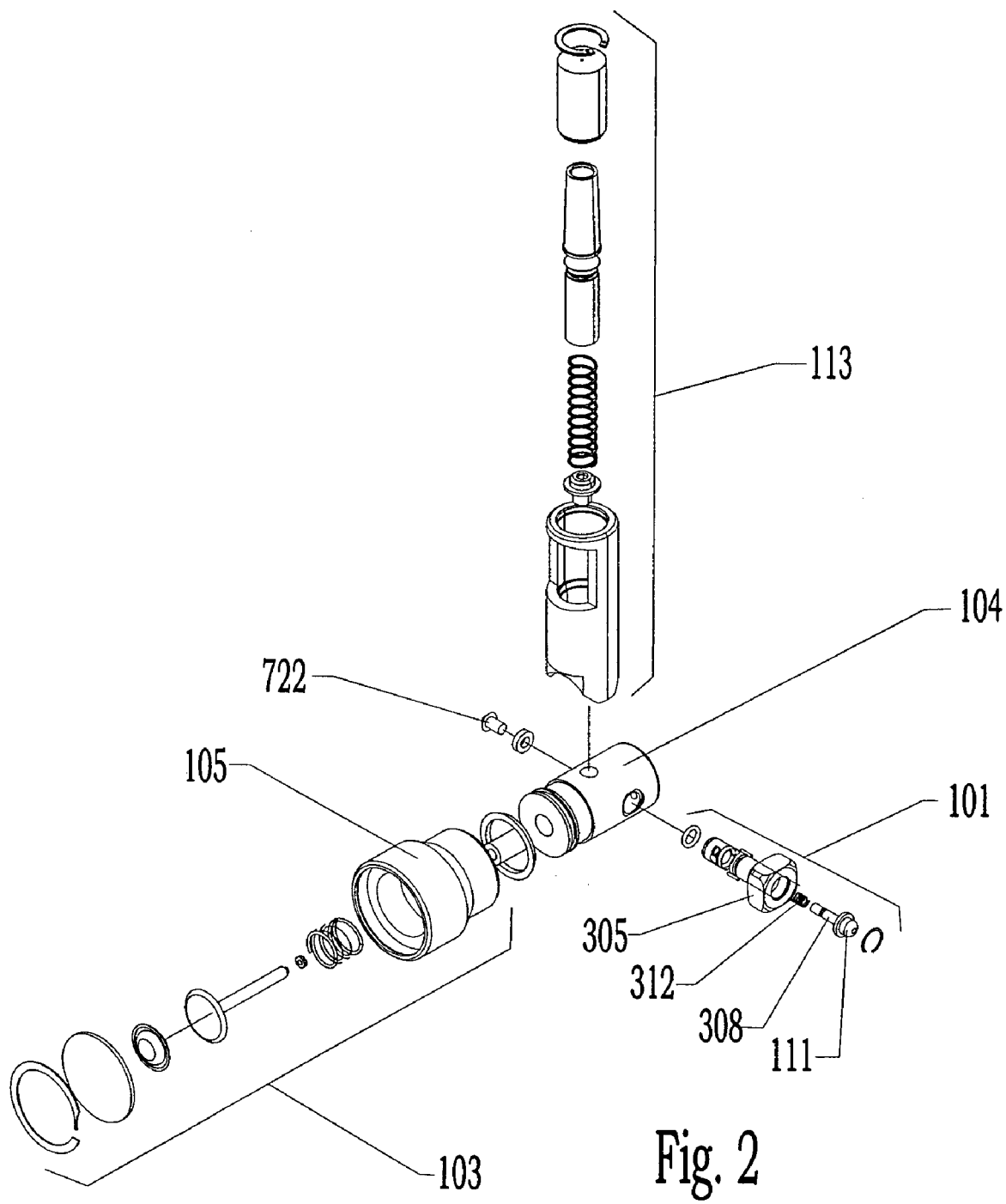
FIG. 2 is an exploded perspective view of the device of FIG. 1.

Referring now to FIGS. 1 and 2, an exemplary embodiment of the present invention is illustrated. As shown in FIG. 1, device 100 comprises a body portion 104 which is coupled to a source of vacuum, such as wall source 102. Spool valve 101 is rotatably coupled to body portion 104 at a side thereof. Regulator 103 having an adjustment knob 105 is coupled to an end of body portion 104. Connection port 106 is also coupled to body portion 104. Additionally, gauge 113 is coupled to body portion 104 and in fluid tight communication with connection port 106 in order to indicate a level of pressure present in a patient vacuum circuit (not shown for simplicity).

Figure 3:
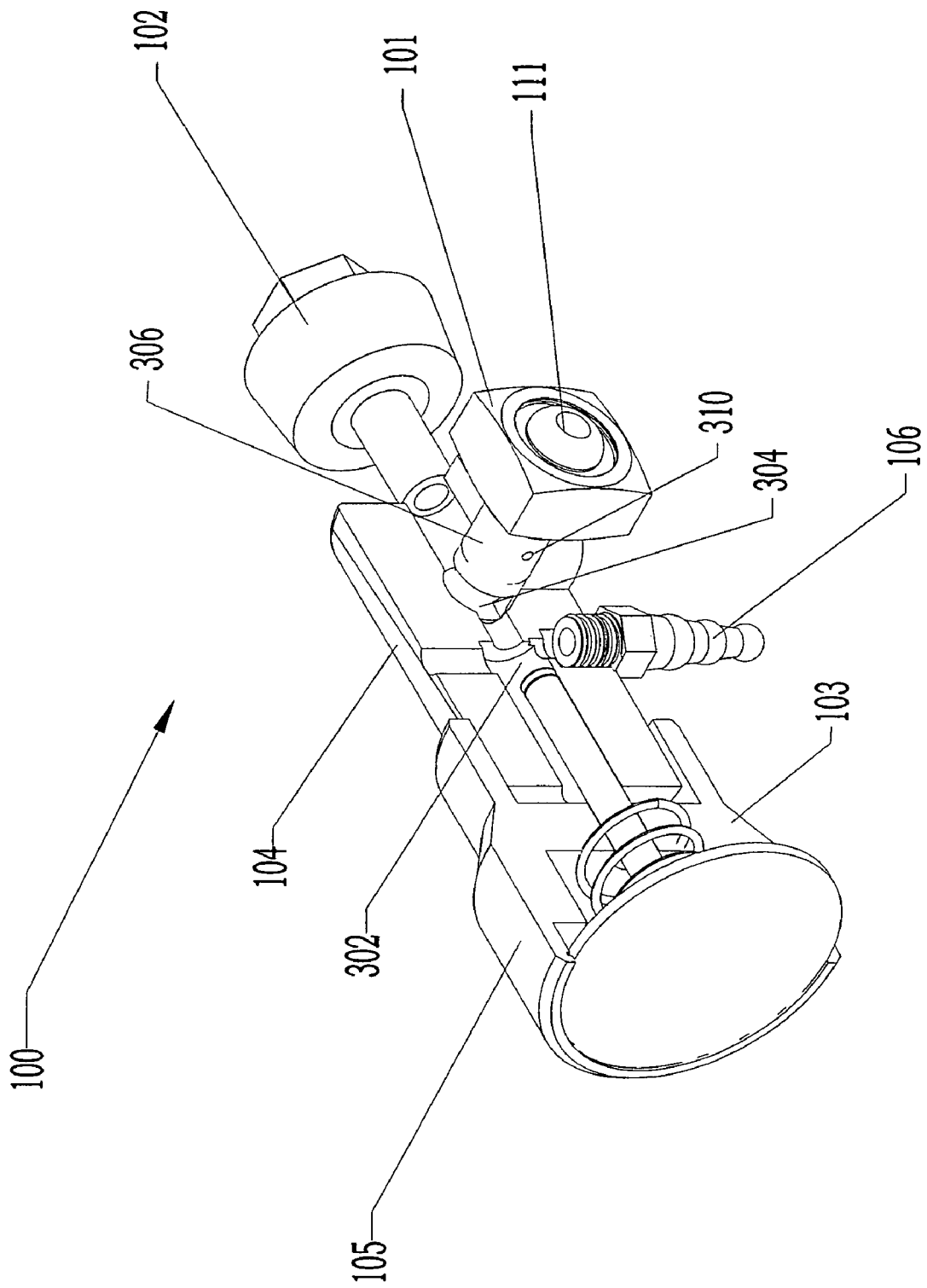
FIG. 3 is a sectional perspective view of a portion of the embodiment of FIG. 1.

In operation, the rotation of spool valve 101 alternatively connects vacuum provided from wall vacuum source 102 or atmospheric pressure from vents (not shown) to body portion 104. In the 'ON' position, as best illustrated in FIG. 3, vacuum from vacuum source 102 is provided to regulation chamber 302 of regulator body 104 via partial circumferential groove 304 which is formed in a portion of shaft 306 of spool valve 101. Regulation chamber 302 is in fluid tight communication with connection port 106 and thus provides vacuum to a patient vacuum circuit (not shown).

Figure 6:
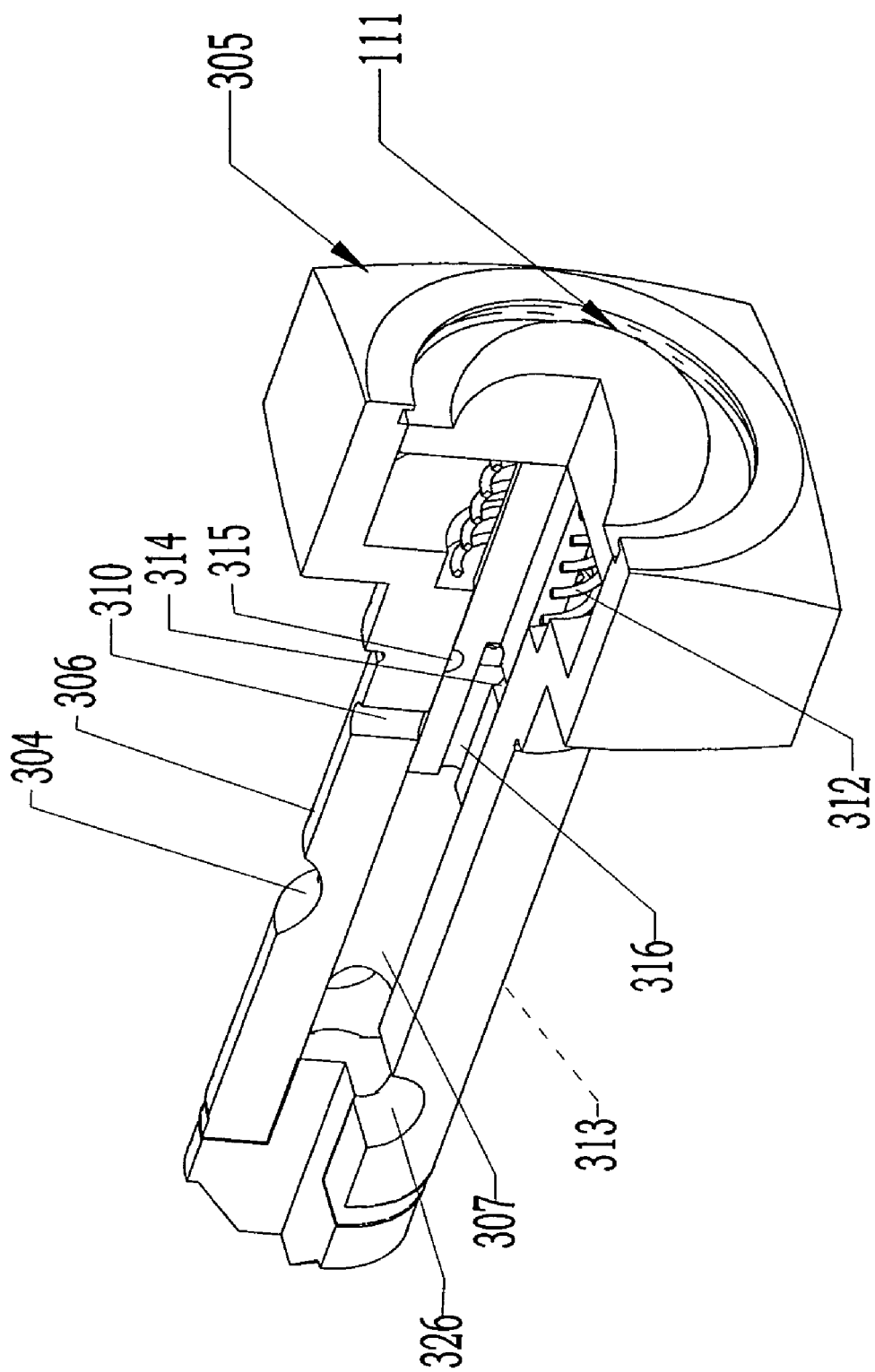
FIG. 6 is an perspective sectioned view of the vacuum selection mechanism of FIG. 4 in the "OFF" position.

When spool valve 101 is in the 'OFF' position (best illustrated in FIG. 6), vacuum from vacuum source 102 is interrupted by shaft 306 of spool valve 101 while a vent port (not shown) disposed in body portion 104 is permitted to communicate with regulation chamber 302 via transverse orifice 326 to thus vent regulation chamber 302 and the patient circuit to atmospheric pressure. In one exemplary embodiment, the vent port is disposed in the rear portion of body portion 104, for example.

Adjustment knob 105 is rotated to regulate the level of vacuum provided from vacuum source 102 to the patient via connection port 106. The amount of regulated vacuum is displayed by gauge 113 as a change in level as viewed though window 114. In the exemplary embodiment shown in FIG. 1, gauge 113 is coupled to a central portion of regulator body 104 and adjacent spool valve 101. Regulator orifice 107 penetrates from an outer surface of body portion 104 into a central portion thereof allowing regulator 103 to leak a controlled amount of atmosphere to maintain a substantially constant vacuum level and vent the patient circuit when the level of regulated vacuum is decreased. Additionally shown in FIG. 1 is a momentary actuator disposed in spool valve 101, depicted as a pushbutton 111 in this embodiment, that will facilitate the methods described herein.

Figure 4:
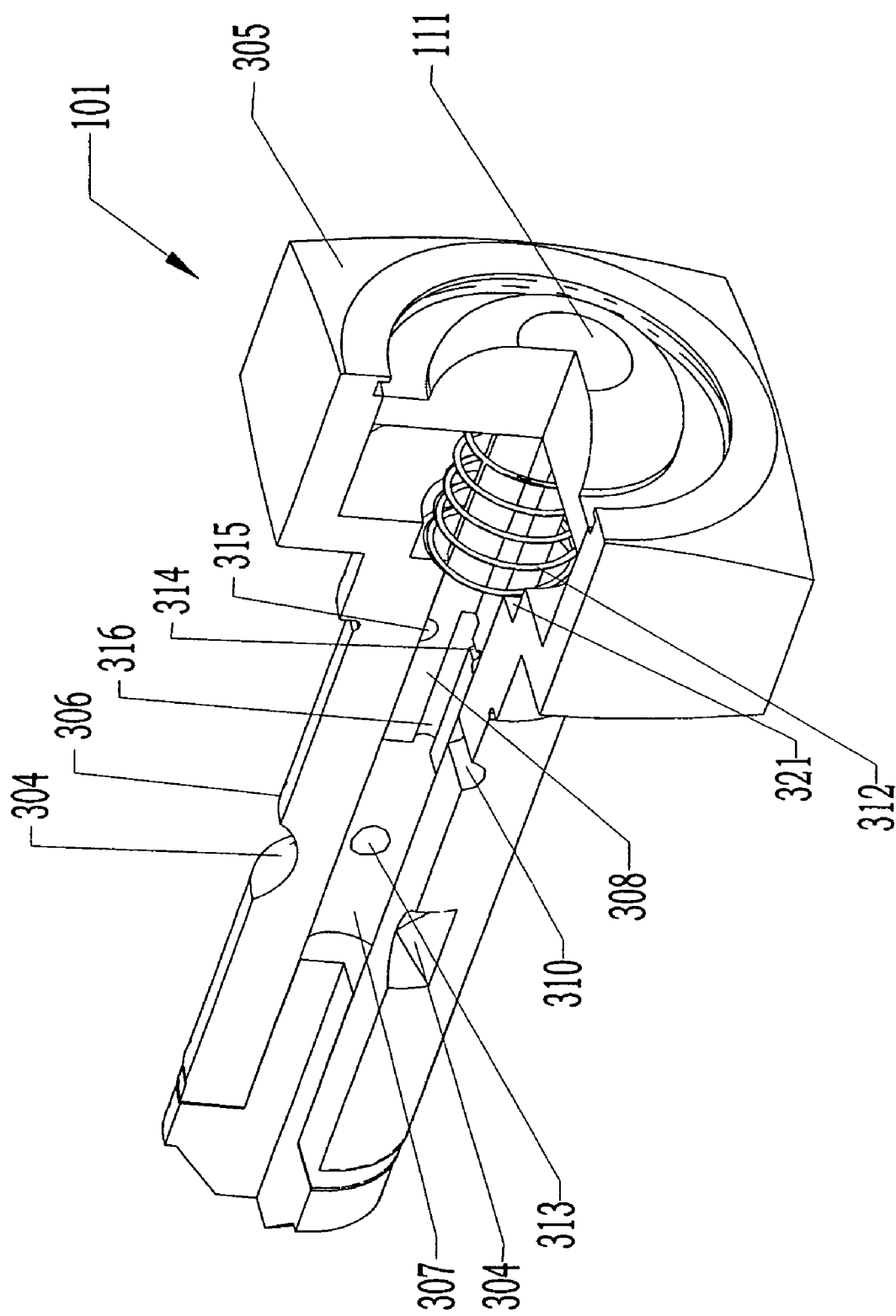
FIG. 4 is a perspective sectioned view of an exemplary vacuum selection mechanism in a standard 'ON' position.

FIG. 4 is a sectional perspective view of an exemplary embodiment of spool valve 101, having been removed from body portion 104 (FIG. 1) for clarity. Spool valve 101 comprises outer shaft 306, having a longitudinal orifice 307 extending though at least a portion of the length of shaft 306, a user accessible end 305 which allows the user to apply or interrupt vacuum applied to the patient circuit by rotating spool valve between an "ON" and an "OFF" position, an inner shaft 308 slidably disposed within longitudinal orifice 307, and a actuator 111 coupled to a distal end of inner shaft 308. A resilient member 312, such as a spring, is disposed over inner shaft 308 and positioned between an inner portion of actuator 111 and a wall portion 321 of spool valve 101 to maintain inner shaft 308 in a normally extended position. Inner shaft 308 comprises a longitudinal orifice 316 extending though at least a portion of the length of inner shaft 308 and is in fluid communication with orifice 314 which extends from an outer portion of inner shaft 308. Orifice 314 also communicates with circumferential groove 315 which extends about the outer portion of inner shaft 308. By providing the combination of orifice 314 in fluid communication with circumferential groove 315, orientation of orifice 314 within longitudinal orifice 307 is not a concern.

In the exemplary embodiment of FIG. 4, channel 304 is formed as circumferential groove disposed about a portion of outer shaft 306 and traversing about 180 degrees. An orifice 313 extends from on outer portion of channel 304 into longitudinal orifice 307. Orifice 313 is oriented such that it is in fluid tight communication with vacuum source 102 when spool valve 101 is in the "ON" position. Another orifice 310 extends from an outer portion of shaft 306 into longitudinal orifice 307. Orifice 310 is oriented such that it is in fluid tight communication with regulation chamber 302 when spool valve 101 is in the "ON" position.

Referring again to FIG. 4, spool valve 101 is shown in the 'ON' position. Regulated fluid flow is allowed to pass from regulation chamber 302 to vacuum source 102 (best shown in FIG. 1) via channel 304. Reduced pressure is provided into elongate interior chamber 307 of spool valve 101 via orifice 313, but flow is absent because, in this position of shaft 306, there is no fluid commutation to regulator chamber 302.

As illustrated in FIG. 4, in the normally extended position of shaft 308, vacuum is communicated into inner longitudinal orifice 316 of inner shaft 308 and to orifice 314 which extends from the outer surface of inner shaft 308 and communicates with inner longitudinal orifice 316. In this case, however, the inner wall of elongate interior chamber 307 prevents further communication of vacuum.

Figure 5:
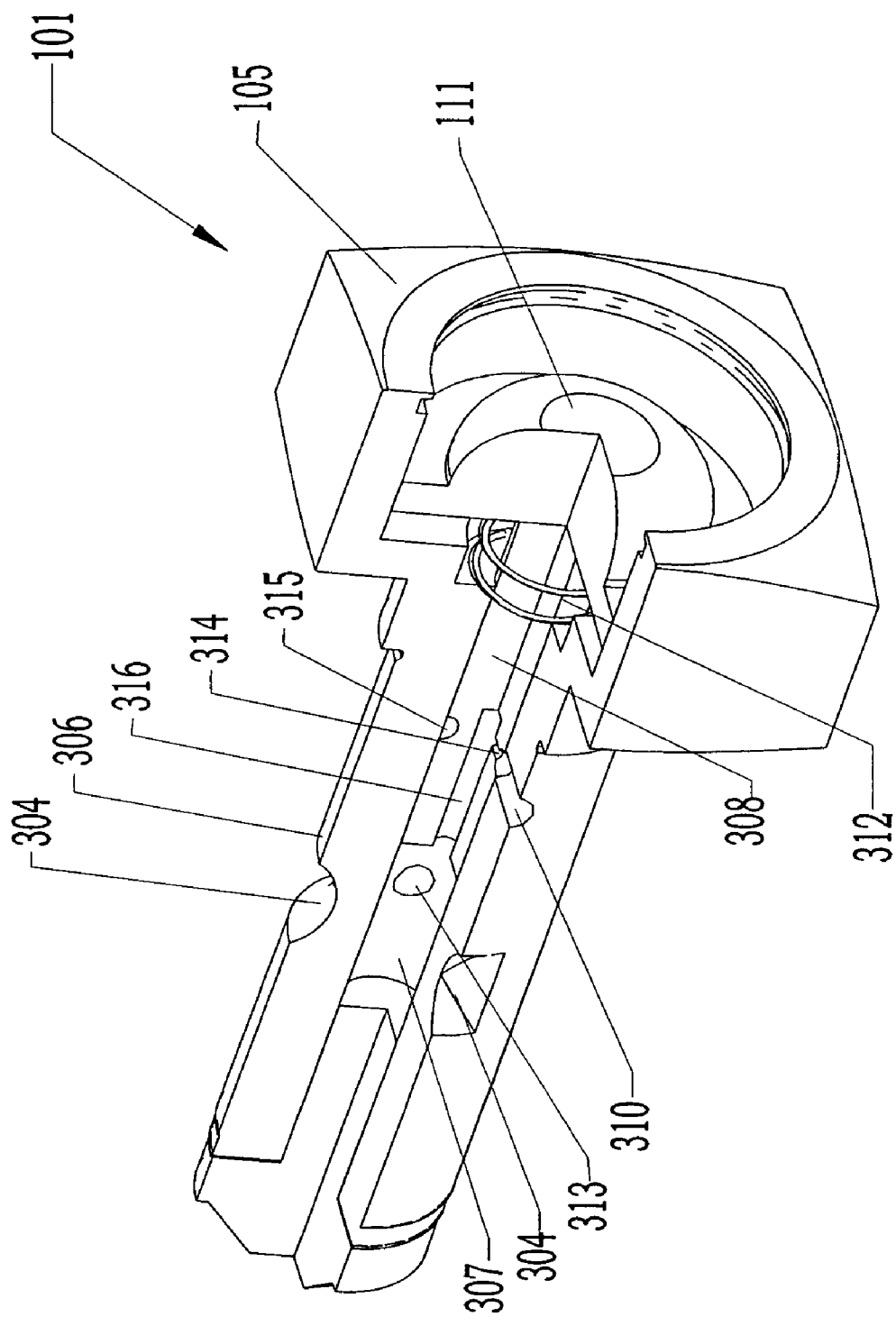
FIG. 5 is a perspective sectioned view of the vacuum selection mechanism of FIG. 4 with the device activated to allow application of temporary increased vacuum.

Referring now to FIG. 5, actuator 111 is shown in a depressed position, thereby allowing longitudinal orifice 316, circumferential groove 315, orifice 314 and orifice 310 to communicate, in tight fluid relation, the decreased pressure in the interior of spool valve 101 with regulation chamber 302. If there is already fluid flow passing from regulation chamber 302 to vacuum source 102 via the path provided by groove 304, the flow restriction provided via orifice 313 have no impact on the regulated vacuum.

Depressing actuator 111 when there is already fluid flow between regulation chamber 302 and vacuum source 102 will have no impact on gauge 113 (best shown in FIG. 1). The absence of movement in gauge 113 indicates that the system is flowing and is not occluded.

If the downstream patient port connection 106 (FIG. 1) or patient circuit is occluded, however, pressing actuator 111 will increase the vacuum in regulator chamber 302 as discussed above with respect to FIG. 5. In this figure the absolute vacuum generated in vacuum chamber 302 will be determined by the relative ratio of effective areas of orifice 313 and regulator orifice 107 (FIG. 1). The absolute fluid flow of the system is dictated by the size of the orifice 313 and the relative pressure differential across it. In one exemplary embodiment, the difference between a normal vacuum level (about 0.6 L/min), based on regulator orifice 107, and the vacuum level applied upon pressing actuator 111 (about 6.0 L/min), based on orifice 313, increases gradually over a predetermined period of time (between about 30 seconds to 1 minute) to generate a high vacuum signal of about greater than about 400 mmHg in the patient circuit.

Gauge 113 will also react to the increase in vacuum in regulator chamber 302. The movement of the gauge indicates the patient circuit coupled to connection port 106 is occluded.

Figure 7:
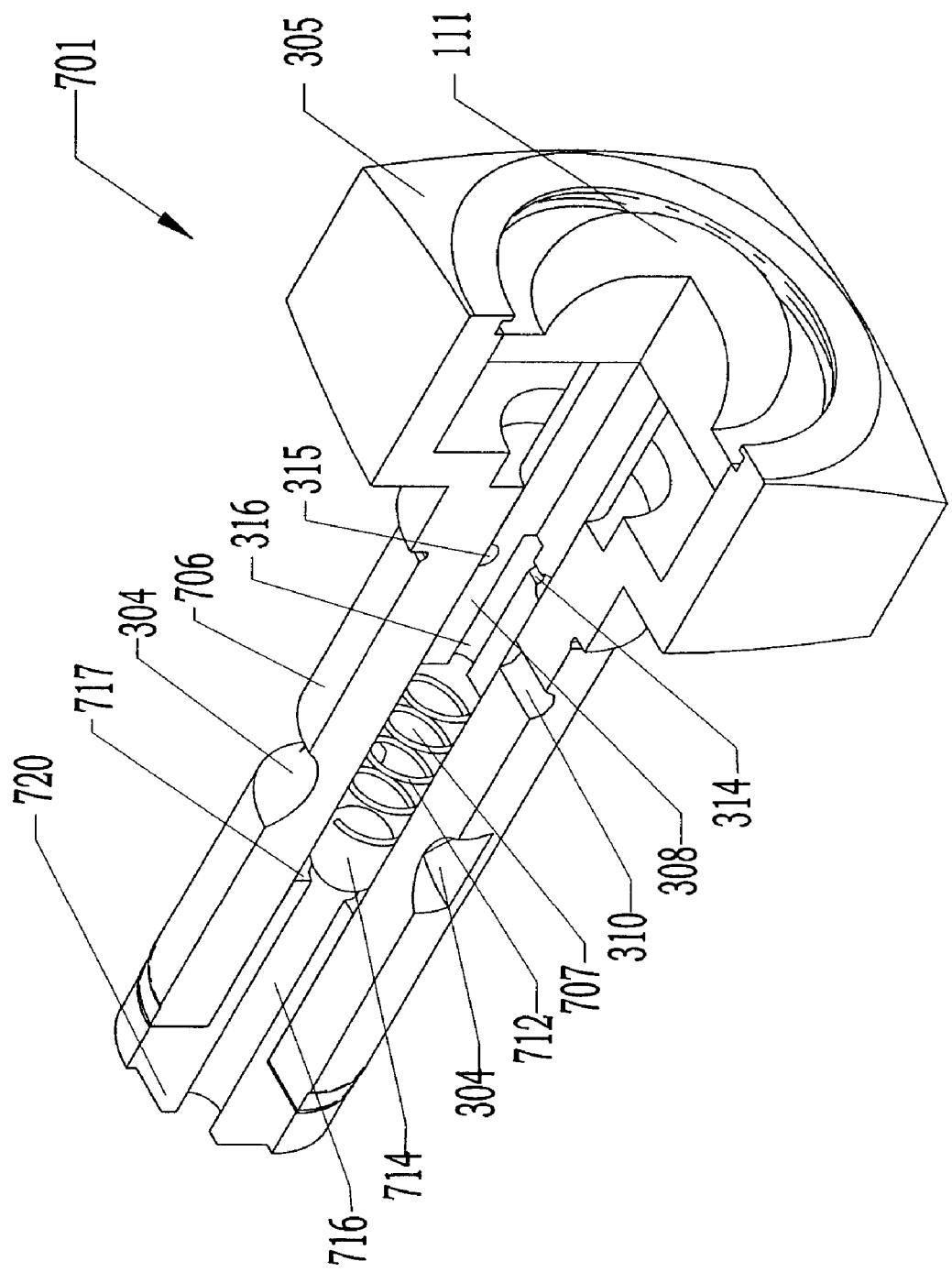
FIG. 7 is a perspective sectioned view of another exemplary vacuum selection mechanism in a standard 'ON' position.

FIG. 7 illustrates a second exemplary embodiment of the present invention. As shown in FIG. 7, spool valve 701, inner shaft 308, and actuator 111 all function similarly as described in the first exemplary embodiment. The decreased pressure in the interior chamber 707 is no longer the same as the vacuum source 102, but rather regulated to another level via an internal pressure regulation mechanism.

In this embodiment, an atmospheric leakage port 716 is formed along a longitudinal axis of outer shaft 706 such that it extends to an end 720 of shaft 706. The end of shaft 706 is coupled to body portion 104 via securing member 722, such as a screw for example (best shown on FIG. 2). To provide a port to atmosphere, securing member 722 has an orifice (not shown) extending along its length. As such, atmosphere communicates through securing member 722 and atmospheric leakage port 716 with interior chamber 707, via resilient member 712 (illustrated as a spring in this embodiment, for example), sealing member 714 (illustrated as a ball in this embodiment, for example), and seat member 717. Pressure from resilient member 712 against sealing member 714, forces sealing member 714 to close against seat member 717, limiting the amount of air allowed in from atmospheric leakage port 716. In this embodiment, the increased vacuum allowed to communicate from interior chamber 707 to regulator chamber 302 is determined by the amount of atmospheric pressure allowed to enter atmospheric leakage port 716.

Similar to the first exemplary embodiment, when spool valve 701 is in the "ON" position and actuator 111 is depressed, longitudinal orifice 316, circumferential groove 315, orifice 314 and orifice 310 to communicate, in tight fluid relation, the decreased pressure in spool valve interior chamber 707 with regulation chamber 302.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A device for providing vacuum to a patient circuit, the device comprising:
    a body portion having i) an interior chamber, ii) an input port, and iii) an output port, and adapted for coupling to a source of the vacuum via the input port;
    a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port; and
    an actuator in fluid communication with said valve, and adapted to move between a first position and a second position while said valve remains in the first position to increase the vacuum in said interior chamber to a second predetermined level.

2. The device of claim 1 wherein said actuator comprises a pushbutton.

3. The device of claim 1 further comprising an orifice disposed in said body portion to provide fluid communication of external atmosphere with said interior chamber when said valve is in said second position.

4. The device of claim 1 wherein said valve has a first axis of rotation and said actuator moves longitudinally along the first axis of rotation.

5. The device of claim 1 wherein the axis of rotation of said valve is substantially perpendicular to a longitudinal axis of the interior chamber.

6. The device of claim 1 further comprising resilient means for normally maintaining said actuator in said first position.

7. The device of claim 6 wherein said resilient means is a spring disposed between a portion of said valve and a portion of said actuator.

8. The device of claim 1 further comprising means for providing atmospheric pressure into said interior chamber when said valve is in said second position.

9. The device of claim 8 wherein said valve comprises a shaft and said means for providing atmospheric pressure is a further orifice extending through said shaft of said valve transverse to said longitudinal axis for providing fluid communication from an exterior of said device to said interior chamber.

10. The device of claim 1 wherein said second predetermined level of vacuum substantially clears said patient circuit of obstructions.

11. A device for providing vacuum to a patient circuit, the device comprising:
    a body portion having i) an interior chamber, ii) an input port, and iii) an output port, and adapted for coupling to a source of the vacuum via the input port;
    a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port;

an actuator in fluid communication with said valve, and adapted to move between a first position and a second position when said valve is in the first position to increase the vacuum in said interior chamber to a second predetermined level; and a further valve rotatably coupled to said body portion; and wherein the output port is coupled to the interior chamber for receiving said first and second predetermined levels of vacuum.

12. The device of claim 11 further comprising an indicator coupled to the body portion to display a level of vacuum provided to the output port.

13. The device of claim 12, wherein said indicator indicates a condition of the patient vacuum circuit.

14. The device of claim 11 wherein said output port is coupled to a central portion of the body portion adjacent said valve.

15. The device of claim 11 wherein said further valve determines at least said first level of vacuum.

16. The device of claim 11 wherein said further valve is a regulator.

17. A device for providing vacuum to a patient circuit, the device comprising:

a body portion having i) an interior chamber, ii) an input port, and iii) an output port, and adapted for coupling to a source of the vacuum via the input port;

a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port; and an actuator in fluid communication with said valve, and adapted to move between a first position and a second position when said valve is in the first position to increase the vacuum in said interior chamber to a second predetermined level, wherein said valve comprises:
  a shaft;
  a first vacuum circuit comprising a groove disposed partially around an outside portion of said shaft, wherein said groove provides fluid communication between said interior chamber and said source of vacuum when said valve is in said first position; and
  a second vacuum circuit comprising:
    a first orifice disposed along at least a portion of said shaft along said longitudinal axis,
    a second orifice disposed in said shaft, oriented transverse to said longitudinal axis and in fluid communication with said first orifice, and
    a third orifice disposed in said shaft, oriented transverse to said longitudinal axis and in fluid communication with said first orifice,
  wherein said second vacuum circuit provides fluid communication between said interior chamber and said source of vacuum when said actuator is in said second.

18. A device for providing vacuum to a patient circuit, the device comprising:

a body portion having i) an interior chamber, ii) an input port, and iii) an output port, and adapted for coupling to a source of the vacuum via the input port;

a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port; and an actuator in fluid communication with said valve, and adapted to move between a first position and a second position when said valve is in the first position to increase the vacuum in said interior chamber to a second predetermined level, wherein said valve comprises a shaft and said means for providing atmospheric pressure comprises:
  an orifice extending from an end of said shaft of said valve along a longitudinal axis thereof;
  a seat formed at a portion of said orifice;
  a sealing member disposed within said orifice and adapted to engage with said seat; and
  a resilient element having a first end disposed against said sealing member distal to said seat,
wherein said orifice provides fluid communication from an exterior of said device to said interior chamber.

19. A device for providing vacuum to a patient circuit, the device comprising:

a body portion having i) an interior chamber, ii) an input port, and iii) an output port, and adapted for coupling to a source of the vacuum via the input port;

a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port; and an actuator in fluid communication with said valve, and adapted to move between a first position and a second position when said valve is in the first position to increase the vacuum in said interior chamber to a second predetermined level, wherein,
  said valve further comprises:
    a shaft; and
    a knob disposed at an end portion of said shaft and adapted to rotate said valve between said first and second positions;
  said actuator further comprises:
    a shaft coaxially coupled to said shaft of said valve,
    a first orifice extending from an end of said shaft and at least partially along an interior of said shaft,
    a circumferential groove disposed along an outside portion of said shaft,
    a second orifice formed in said circumferential groove, transverse to said first orifice and in fluid communication with said first orifice,
  wherein said actuator provides fluid communication between said interior chamber and said source of vacuum via i) said first orifice, ii) said circumferential groove and iii) said second orifice when said actuator is in said second position.

20. A device for providing vacuum to a patient circuit, the device comprising:

a body portion having i) an interior chamber, ii) an input port, and iii) an output port, and adapted for coupling to a source of the vacuum via the input port;

a valve moveably coupled to said body portion, said valve selectable between i) a first position in which the vacuum is provided to said interior chamber via said valve to flow to the output port at a first predetermined level and ii) a second position in which the vacuum is interrupted to said interior chamber and the output port; and an actuator in fluid communication with said valve, and adapted to move between a first position and a second position when said valve is in the first position to increase the vacuum in said interior chamber to a second predetermined level;

wherein said valve further comprises a shaft and a knob disposed at an end portion of said shaft and adapted to rotate said valve between said first and second positions.

* * * * *